United States Patent
Jenkins et al.

(10) Patent No.: US 7,640,136 B2
(45) Date of Patent: Dec. 29, 2009

(54) SYSTEM AND METHOD FOR DETERMINATION OF OBJECT LOCATION FOR CALIBRATION USING PATIENT DATA

(75) Inventors: John H. Jenkins, Grand Prairie, TX (US); Khalid Bouissaghouane, Amersfoort (NL)

(73) Assignee: General Electric Company, Schenectady, NY (US)

( * ) Notice: Subject to any disclaimer, the term of this patent is extended or adjusted under 35 U.S.C. 154(b) by 330 days.

(21) Appl. No.: 11/401,135

(22) Filed: Apr. 10, 2006

(65) Prior Publication Data

US 2007/0239395 A1    Oct. 11, 2007

(51) Int. Cl.
*G06F 19/00* (2006.01)

(52) U.S. Cl. .................. 702/158; 702/85; 702/166; 702/173; 378/4; 378/20; 378/207

(58) Field of Classification Search ............... 702/160, 702/166, 173; 378/210, 18, 150, 207, 4, 378/20, 209, 901, 205, 69; 382/128; 128/922
See application file for complete search history.

(56) References Cited

U.S. PATENT DOCUMENTS

| | | | | | |
|---|---|---|---|---|---|
| 4,787,098 | A | * | 11/1988 | Silver | 378/18 |
| 4,809,172 | A | * | 2/1989 | Hopkinson et al. | 378/4 |
| 5,241,966 | A | * | 9/1993 | Finkelstein et al. | 600/485 |
| 5,825,843 | A | * | 10/1998 | Kobayashi | 378/20 |
| 2003/0194057 | A1 | * | 10/2003 | Dewaele | 378/210 |

OTHER PUBLICATIONS

Vaillant et al., "A new calibration approach for quantification application in the cathlab," International Congress Series 1268 (2004) 1040-1044.

* cited by examiner

*Primary Examiner*—Drew A Dunn
*Assistant Examiner*—Hien X Vo
(74) *Attorney, Agent, or Firm*—Hanley, Flight & Zimmerman, LLC

(57) ABSTRACT

Certain embodiments of the present invention provide methods and systems for determining a location of an object of interest for use in image calibration. Certain embodiments of a method include loading an image of at least a portion of a patient. The image includes an object of interest. The method further includes retrieving patient data related to the patient, and automatically generating a proposed height value of the object of interest in relation to a reference location. The proposed height value is generated by selecting a height value from a set of height values based on the patient data. In certain embodiments, the reference location is a positioning tabletop. In certain embodiments, the patient data includes patient height and/or patient weight, and the set of height values is indexed based on height and/or weight by gender.

18 Claims, 3 Drawing Sheets

Regression chart for males:  Regression Plot
Y = 151.538 − 21.08899X
R-Sq = 68.5%

Regression chart for females:  Regression Plot
Y = 126.386 − 14.5294X
R-Sq = 73.1%

SYSTEM AND METHOD FOR DETERMINATION OF OBJECT LOCATION FOR CALIBRATION USING PATIENT DATA

BACKGROUND OF THE INVENTION

The present invention generally relates to imaging system calibration. In particular, the present invention relates to object positioning and calibration of an imaging system.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as x-rays passing through a patient, for example. The generated images may be used for many purposes. For instance, internal defects in an object may be detected. Additionally, changes in internal structure or alignment may be determined. Fluid flow within an object may also be represented. Furthermore, the image may show the presence or absence of objects in an object. The information gained from medical diagnostic imaging has applications in many fields, including medicine and manufacturing.

In order to help ensure that medical diagnostic images are reliable, it is advantageous to calibrate medical diagnostic imaging systems. The calibration of imaging systems is important for several reasons, including image quality, measurement accuracy and system performance. Poor image calibration may prevent reliable analysis of an image. The calibration of medical imaging systems may help to produce a distinct and usable representation of an object.

Inaccuracies in an imaging system may result in blurring, streaking, or introduction of ghost images or artifacts in the resulting image. For example, if a detector position or the center of a medical imaging system is inaccurate, an x-ray will be projected at an incorrect angle and produce an error in the resulting image. Thus, a need exists for a method and apparatus for more accurate calibration of a medical diagnostic imaging system.

In a cathlab, for example, a physician needs fast and accurate angiographic methods in order to minimize the time spent on determining quantitative information. Traditional quantification procedures are often unsatisfactory because they require using a well-known object as reference (for example, a catheter or calibration sphere) for each frame to calibrate. These steps are time consuming and not do carry clinical value. Even if catheter calibration has eased the procedure, accuracy and precision constraints have to be considered with care. Indeed, an error of percentage in the catheter size, which may be due to the catheter manufacturer, corresponds to an equivalent error in the vessel size for vessel quantification. Current calibration methods may be automatic except for entering the height of the element of interest above the table, which is not a priori known.

The growth of interventional procedures drives the development of simple, fast and accurate quantification methods. Quantification is used to assess the volume of a left ventricle, for example, but also for choosing the size of a stent or a balloon during the course of a revascularization procedure. However, in numerous occasions, the therapeutic procedures are executed within the same session as the diagnosis, and the physician seeks to minimize the time spent on determining quantitative information such as the diseased artery reference diameter or the lesion length.

In most cases in the cathlab, a vessel dimension is computed by multiplying its apparent size in the image by a calibration factor expressed in millimeters per pixel. Usually, this calibration factor is determined by considering the apparent size of a reference object of known size. Generally, the reference object is the catheter. This method requires a user to perform operations not directly related to the clinical objective, such as obtaining an image frame including the catheter, either edge detecting or depositing one or two points on the catheter, and entering the size of the catheter. In addition, accuracy and precision constraints have to be taken into account. The size of the catheter has to be known very precisely. An error of 5% in this parameter corresponds to an error of the same magnitude in the vessel size, for example. The catheter and the vessel under analysis have to be in a plane parallel to the image plane.

Several recent imaging systems, such as the GE Innova, Advantage Workstation, and CA1000, have introduced or will introduce an auto calibration feature to improve the effectiveness of image analysis due to an increase in efficiency of operation. An efficiency increase is achieved by provide user access to a system calibration without having to stop an imaging workflow, obtain an image, and then measure a separate target for calibration. Currently, however, the auto calibration feature requires an input variable representing a height of a proposed body part above a positioning table (effectively, the distance away from the geometric "isocenter" of the x-ray beam). The height input variable is either accepted as a default value or is input by the user. Since the tabletop distance is recorded in the image data, the height is correlated with the isocenter distance). This means the auto calibration has either a manual step that makes the system un-necessarily slower and/or a default value that has some inaccuracy potential. Additionally, current methods of calibration do not account for differences in patient body type, with corresponding differences in position for an object to be imaged.

Therefore, a need exists for systems and methods for calibration of an image acquisition system. A need exists for systems and methods for improved auto-calibration of an image acquisition system. Furthermore, a need exists for systems and methods for calibration based on organs, as well as catheters and blood vessels, to be imaged. Systems and methods accommodating a variety of patient body types and objects to be imaged would be highly desirable.

BRIEF SUMMARY OF THE INVENTION

Certain embodiments of the present invention provide methods and systems for determining a location of an object of interest for use in image calibration. Certain embodiments of a method include loading an image of at least a portion of a patient. The image includes an object of interest. The method further includes retrieving patient data related to the patient, and automatically generating a proposed height value of the object of interest in relation to a reference location. The proposed height value is generated by selecting a height value from a set of height values based on the patient data.

In certain embodiments, the reference location is a positioning tabletop. In certain embodiments, a user is allowed to approve and/or edit the proposed height value, for example. In certain embodiments, the proposed height value may be used in calibration for a region of interest in an image. In certain embodiments, the patient data includes patient height and/or patient weight, and the set of height values is indexed based on height and/or weight by gender. In certain embodiments, patient data also includes patient age, and the set of height values is further indexed based on age by gender. In certain embodiments, the height value corresponds to a chest size determined by correlating a ratio of patient height to patient weight for a certain gender.

Certain embodiments provide a system including a patient data record including patient data related to at least one patient and a processor capable of automatically generating a proposed height value for an object of interest in an image in relation to a reference location. The proposed height value is generated by selecting a height value from a set of height values based on the patient data.

Certain embodiments provide a computer readable medium having a set of instructions for execution on a computing device. The set of instructions includes a patient data record including patient data related to at least one patient and an object height determination routine for generating a proposed height value for an object of interest in an image in relation to a reference location. The proposed height value is generated by selecting a height value from a set of height values based on the patient data, for example.

Figure 1:
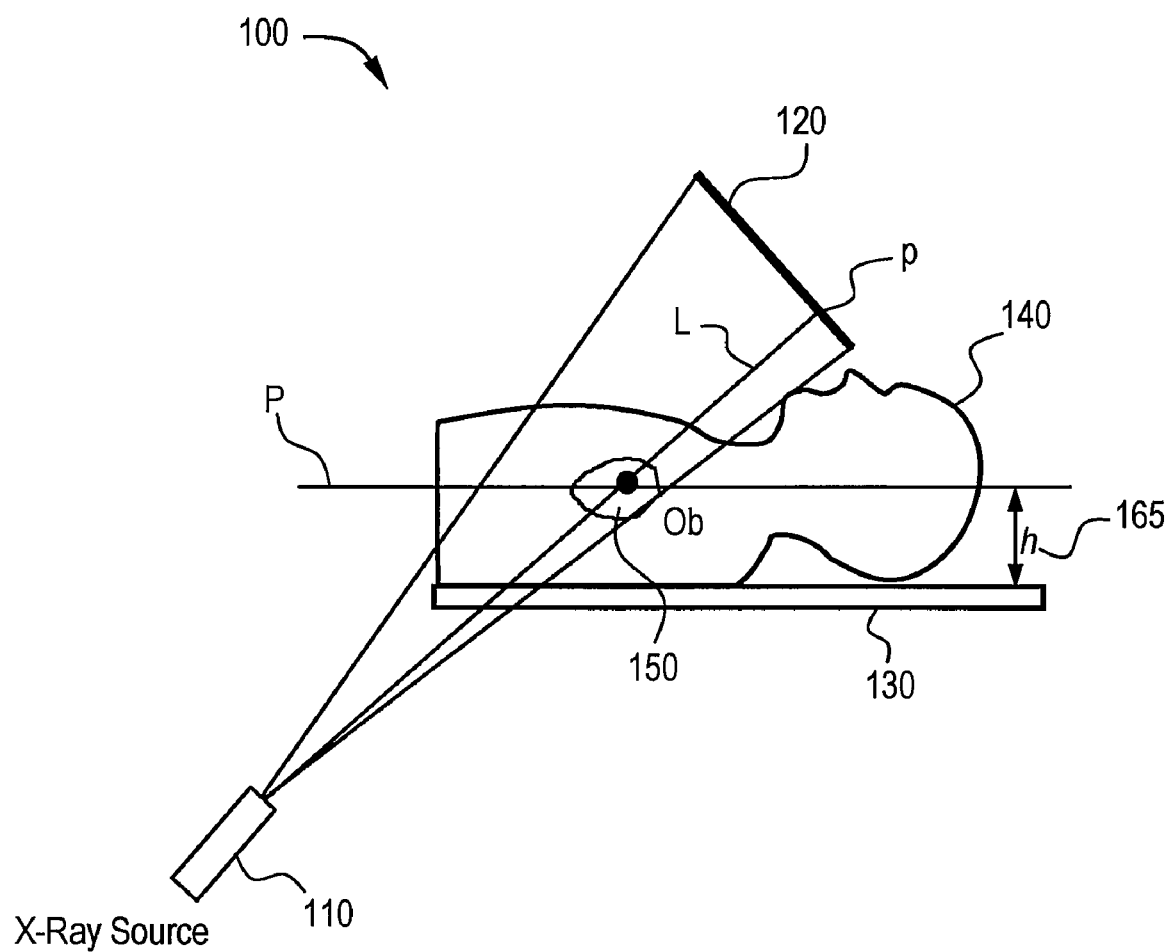
FIG. 1 illustrates an exemplary imaging system used in accordance with an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

FIG. 1 illustrates an imaging system 100 used in accordance with an embodiment of the present invention. For purposes of illustration, FIG. 1 and certain embodiments of the present invention are described in relation to an x-ray imaging system but may also apply to a plurality of other modalities. The system 100 includes a source 110, a detector 120, a positioning surface 130, and a patient 140. The patient includes an object of interest 150 for imaging and/or other analysis. A height 165 represents a distance between a center of the object 150 and the positioning surface 130. The positioning surface 130 may be an operating table, for example. For example, FIG. 1 illustrates a relationship of the patient 140, in a supine position on a cathlab table 130, and the imaging system 100 with the source 110 below and the detector 120 (e.g., an Innova flat panel detector) above the patient 140 on a movable gantry. The object 150 of interest in this case is the heart, for example.

A calibration factor may be calculated to determine a relation between an apparent size and an actual size of the object of interest 150. The calibration factor may be obtained from a geometric model of the system 100, for example. For example, the gantry is modeled as a concurrent three orthogonal axis mechanical system. The calibration factor may be determined based on the position of the object 150 in the body 140. The position of the object 150 may be determined for calibration in images, such as projection x-ray images, using patient data.

A position of an X-ray source 110 focal point may be determined from a known source-to-isocenter distance. An isocenter is a center of rotation of an acquisition system being used (a center of rotation between a source 110 and detector 120, for example). A spatial location and orientation of an image detector 120 may be defined by a rotation angle of the gantry and the source-image distance, for example. A location of the table 130, which supports the patient 140, is defined by three translation parameters, for example. A location of the object of interest 150 in the patient 140 may be determined as described further below. Based on these results, the physician may plan for a surgical procedure, decide on the size of the interventional tools to be used, and/or determine if other calibration strategies may be applied, for example.

Certain embodiments take into account existing information about the patient, to determine the anthropometric relationships of the data and automatically offer a proposed "height above bare table top" to the auto calibration system. The existing information includes a patient's height, weight, and sex, for example. The object height calculation provides a "default" value based on a calculation of patient size. A user may accept or edit the generated value. The calculation based on height (and possibly weight and/or other parameter) for a given gender provides a more acceptable and customizable patient size for more accurate location of the object 150 of calibration interest in an image reference space. By accepting this value that changes appropriately with each patient and not having to input the value from manual measurement or visual estimation of body size or reliance on a global "average," auto calibration algorithms may be more repeatable, more accurate, and more automatic, for example.

As discussed above, existing patient information is used to deduce the calibration object location value. A relationship between the sex of the patient and the patient's weight and/or height, for example, is calculated to determine the height or position of the organ to be imaged for use in an auto calibration algorithm. Other information, such as patient age, may be used as well. Further, a user may easily override the suggested value by inputting a replacement value by editing the dialog with a modified value, a measured value and/or other value of his or her own choosing.

Figure 3:
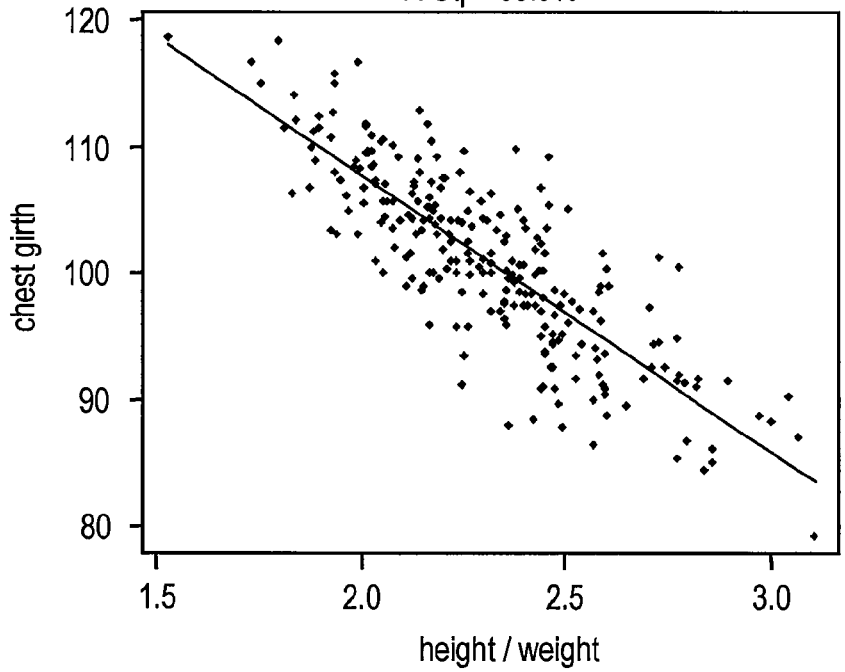
FIG. 3 shows exemplary regression plots of representative measurement relationships between chest girth, height/weight and gender.
Figure 3:
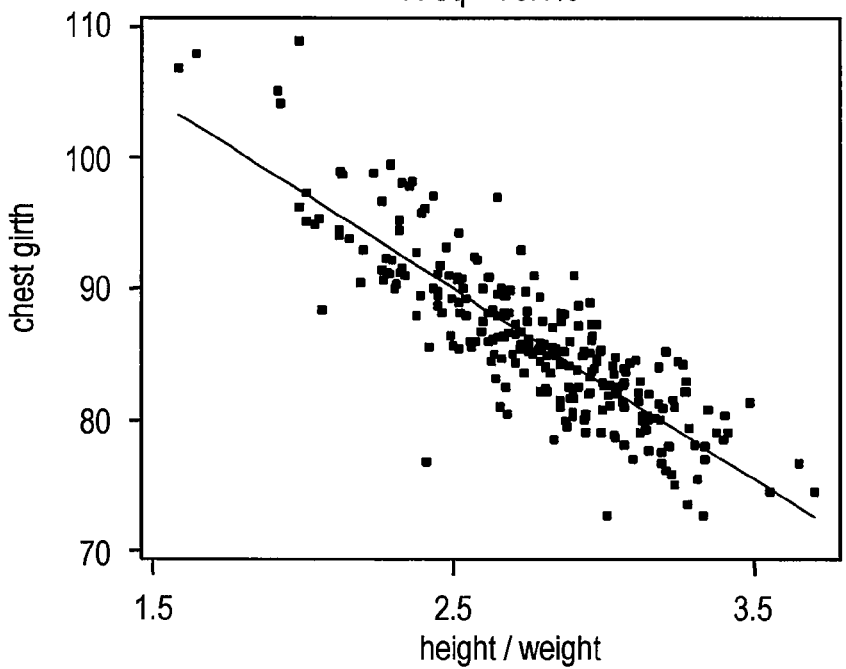

Certain embodiments derive a relationship between patient gender and patient data such as height and weight, for example, from anthropometric measurements of a plurality of men and women, as shown for example in FIG. 3. Measurement data is used to establish a relationship of chest girth to the patient data (e.g., height and weight) of both men and women, as distributed in this sampled group. Certain embodiments provide an ability to take existing and readily available patient information and establishing what the chest girth should be by including the relationship of patient data such as height to weight to further define and refine the missing variable for the calibration calculation.

Thus, certain embodiments determine, by gender, average mid-chest size for a given height (and possibly for a given weight and/or other information). In certain embodiments, size may be determined using additional patient data, such as patient age, for example. A user, such as a surgeon, physician, and/or other healthcare personnel, is presented with a size for a given patient, based on that patient's information, and the user confirms or adjusts that value, rather than being limited to a generic average value.

Alternatively, the value determined by the system may be automatically confirmed and used without user interaction.

Once the size/position value is confirmed, the value is supplied to a calibration algorithm. For example, the object of interest may be calibrated at a certain number of pixels per millimeter. Then, a volume of the object 150 to be imaged in the patient 140, such as a heart, may be determined, for example. Based on object volume, a number of pixels in the object of interest in the image may be converted or scaled to a representation of actual size.

For example, a calibration may involve a projection p of an object 150 of interest in an image. The object 150 is located on a geometric line L, which runs from the imaging focal spot to the projection point p. A horizontal plane P is situated at a height h over the table 130. The height h is the height of the object of interest 150 in the patient 140 with respect to the tabletop 130, as determined above. As shown in FIG. 1, the intersection between the line L and the plane P defines the location of the object of interest 150. A calibration factor may be computed by a variety of methods, including Thales theorem, for example.

After calibration has been completed, medical personnel may use the imaging system and/or images produced in the system for a variety of applications. For example, further images may be obtained, obtained images may be used in non-invasive or invasive procedures such as cardiac catheterization, surgical navigation and/or surgical planning may be executed, and/or other medical procedure(s) may be performed. Image data may be processed based on the computed calibration factor, for example.

Figure 2:
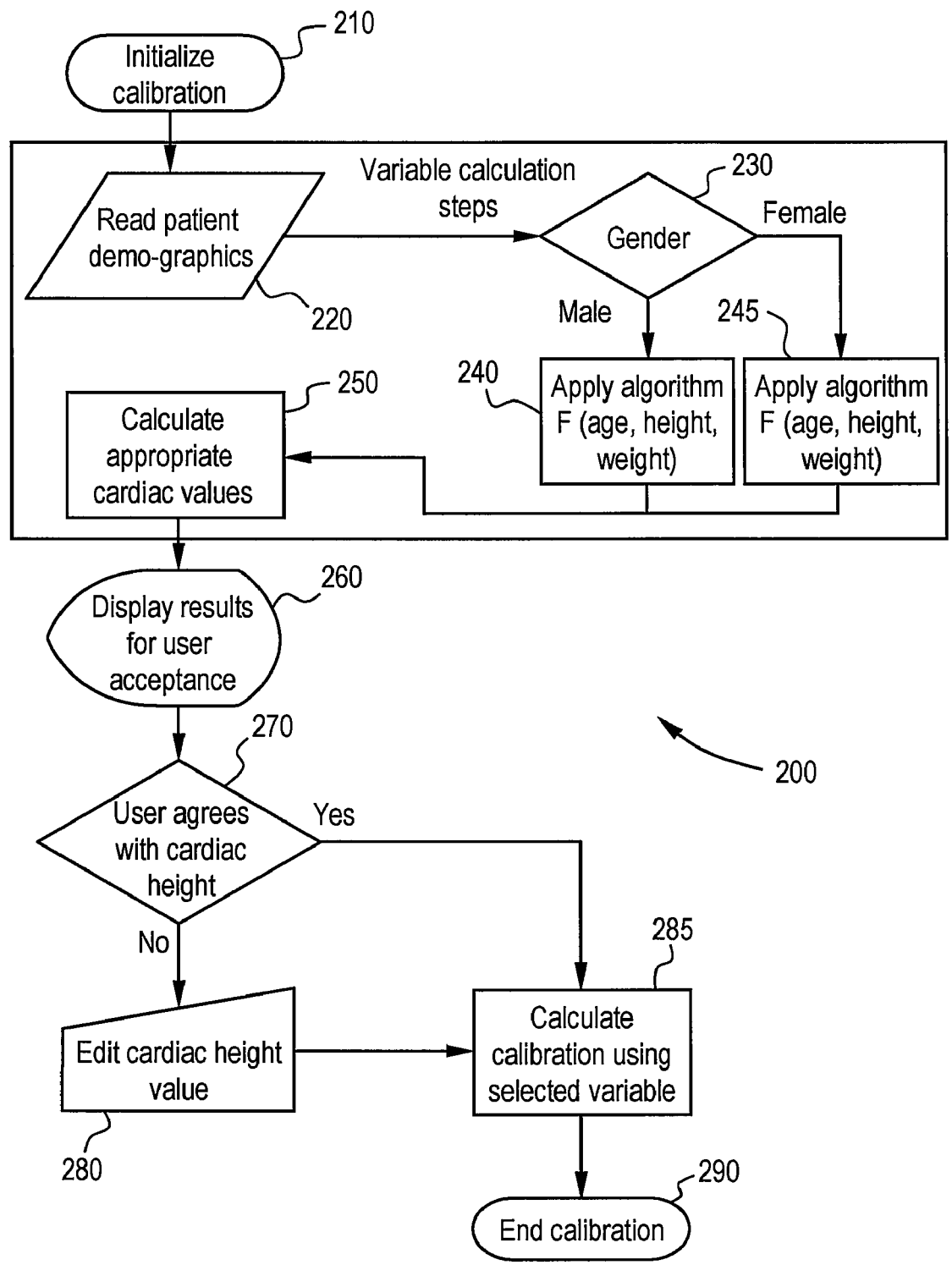
FIG. 2 illustrates a flow diagram for a method for object location determination for calibration in accordance with an embodiment of the present invention.

FIG. 2 illustrates a flow diagram for a method 200 for object location determination for calibration in accordance with an embodiment of the present invention. First, at step 210, calibration is initialized. Then, at step 220, patient demographic data is read. Next, at step 230, patient gender is determined from the demographic data. If the patient is male, then, at step 240, a male calibration algorithm is applied as a function of the patient's age, height, and/or weight, for example. If the patient is female, then, at step 245, a female calibration algorithm is applied as a function of the patient's age, height, and/or weight, for example.

At step 250, appropriate calibration value(s) are calculated based on the function applied in step 240 or step 245. Then, at step 260, the values(s) are displayed for user acceptance. Next, at step 270, user acceptance is determined. If the user does not agree with the calculated value(s), then, at step 280, the user edits the calculated value(s). At step 285, calibration proceeds using the selected calibration value(s). Finally, at step 290, calibration ends and regular system operation may proceed.

For example, a female height and weight are retrieved from a patient record and are compared to determine a ratio, such as 2.5. Using the histogram data in FIG. 3, a female height/weight ratio of 2.5 corresponds to a chest girth of 90 cm. The chest girth value may be used to determine a calibration value for an object of interest in the chest, such as the heart. Then, the value is presented to a user. The user may accept the value or modify the value. Alternatively, the imaging system may automatically use the value without user input. Calibration then proceeds using the calibration value. Following calibration, calibrated images may be used for a variety of purposes.

One or more of the steps of the method 200 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments accommodate a variety of patient body types and objects to be imaged within a patient. Certain embodiments increase speed of auto calibration usage while making a more accurate estimation of the size of the patient being measured.

In certain embodiments, calibration may be performed separately for different regions of interest in a patient. For example, in FIG. 1, a patient's chest bones and heart may be projected on the same spot on an imaging acquisition device but may have different calibration factors.

Additionally, in certain embodiments, calibration is independent of imaging system parameters and does not affect imaging system parameters. Rather, calibration is a sizing of objects of interest in the body in projection images.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for determining a location of an object of interest for use in image calibration, said method comprising:
    loading an image of at least a portion of a patient, said image including an object of interest;
    retrieving patient data related to said patient, said patient data used to define, at least in part, a patient body type for said patient;
    automatically generating a proposed height value of said object of interest in relation to a reference location, said proposed height value of said object of interest generated by selecting a height value from a set of height values based on said patient data, said proposed height value of said object of interest corresponding to a height of said object of interest in relation to said reference location based at least in part on said patient data; and
    providing an option for a user to at least one of approve and edit said proposed height value.

2. The method of claim 1, wherein said reference location comprises a positioning table top.

3. The method of claim 1, further comprising using said proposed height value in image calibration.

4. The method of claim 1, wherein said patient data comprises at least one of patient height and patient weight and wherein said set of height values is indexed based on at least one of height and weight by gender.

5. The method of claim 4, wherein said patient data further comprises patient age and wherein said set of height values is further indexed based on age by gender.

6. The method of claim 1, wherein said height value corresponds to a chest size determined by correlating a ratio of patient height to patient weight for a certain gender.

7. A system for image calibration, said system comprising:
a patient data record including patient data related to at least one patient, said patient data used to define, at least in part, a patient body type for said patient; and
a processor configured to automatically generate a proposed height value for an object of interest of said patient in an image in relation to a reference location, said proposed height value for said object of interest generated by selecting a height value from a set of height values based on said patient data, said proposed height value of said object of interest corresponding to a height of said object of interest in relation to said reference location based at least in part on said patient data,
wherein the processor allows a user to at least one of approve and edit said proposed height value.

8. The system of claim 7, wherein said reference location comprises a positioning table top.

9. The system of claim 7, further comprising using said proposed height value in image calibration.

10. The system of claim 7, wherein said patient data comprises at least one of patient height and patient weight and wherein said set of height values is indexed based on at least one of height and weight by gender.

11. The system of claim 10, wherein said patient data further comprises patient age and wherein said set of height values is further indexed based on age by gender.

12. The system of claim 7, wherein said height value corresponds to a chest size determined by correlating a ratio of patient height to patient weight for a certain gender.

13. A tangible computer readable storage medium having a set of instructions for execution on a computing device, said set of instructions comprising:
a patient data record including patient data related to at least one patient, said patient data used to define, at least in part, a patient body type for said patient; and
an object height determination routine for generating a proposed height value for an object of interest in an image in relation to a reference location, said proposed height value for said object of interest generated by selecting a height value from a set of height values based on said patient data, said proposed height value of said object of interest corresponding to a height of said object of interest in relation to said reference location based at least in part on said patient data, said height determination routine allowing for a user to at least one of approve and edit said height value.

14. The tangible computer readable storage medium of claim 13, wherein said reference location comprises a positioning table top.

15. The tangible computer readable storage medium of claim 13, further comprising an image calibration routine using said proposed height value in image calibration.

16. The tangible computer readable storage medium of claim 13, wherein said patient data comprises at least one of patient height and patient weight and wherein said set of height values is indexed based on at least one of height and weight by gender.

17. The tangible computer readable storage medium of claim 16, wherein said patient data further comprises patient age and wherein said set of height values is further indexed based on age by gender.

18. The tangible computer readable storage medium of claim 13, wherein said height value corresponds to a chest size determined by correlating a ratio of patient height to patient weight for a certain gender.

* * * * *

UNITED STATES PATENT AND TRADEMARK OFFICE
CERTIFICATE OF CORRECTION

| | |
|---|---|
| PATENT NO. | : 7,640,136 B2 |
| APPLICATION NO. | : 11/401135 |
| DATED | : December 29, 2009 |
| INVENTOR(S) | : Jenkins et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 533 days.

Signed and Sealed this

Ninth Day of November, 2010

David J. Kappos
*Director of the United States Patent and Trademark Office*